US010052067B2

(12) United States Patent
Zhang

(10) Patent No.: US 10,052,067 B2
(45) Date of Patent: Aug. 21, 2018

(54) WEARABLE DEVICE

(71) Applicant: Huawei Technologies Co., Ltd., Shenzhen (CN)

(72) Inventor: Hong Zhang, Shenzhen (CN)

(73) Assignee: Huawei Technologies Co., Ltd., Shenzhen (CN)

(*) Notice: Subject to any disclaimer, the term of this patent is extended or adjusted under 35 U.S.C. 154(b) by 0 days.

(21) Appl. No.: 15/554,122

(22) PCT Filed: Feb. 28, 2015

(86) PCT No.: PCT/CN2015/073411
§ 371 (c)(1),
(2) Date: Aug. 28, 2017

(87) PCT Pub. No.: WO2016/134540
PCT Pub. Date: Sep. 1, 2016

(65) Prior Publication Data
US 2018/0042550 A1 Feb. 15, 2018

(51) Int. Cl.
G08C 19/22 (2006.01)
H04Q 9/00 (2006.01)
A61B 5/00 (2006.01)
G06F 1/16 (2006.01)
G06F 1/32 (2006.01)
G06F 3/048 (2013.01)

(52) U.S. Cl.
CPC .............. *A61B 5/681* (2013.01); *G06F 1/163* (2013.01); *G06F 1/1694* (2013.01); *A61B 5/0004* (2013.01); *G06F 1/3206* (2013.01); *G06F 3/048* (2013.01)

(58) Field of Classification Search
CPC ....... H04M 1/7253; H04W 4/80; Y02D 70/00
USPC .................................................. 340/870.07
See application file for complete search history.

(56) References Cited

U.S. PATENT DOCUMENTS

| 2013/0197680 A1 | 8/2013 | Cobbett et al. |
| 2013/0208938 A1 | 8/2013 | Midha |
| 2014/0070957 A1 | 3/2014 | Longinotti-Buitoni et al. |
| 2014/0106677 A1* | 4/2014 | Altman ............... H04B 1/3827 455/41.2 |
| 2014/0249760 A1 | 9/2014 | Proud et al. |

(Continued)

FOREIGN PATENT DOCUMENTS

| CN | 101978374 A | 2/2011 |
| CN | 103169448 A | 6/2013 |

(Continued)

*Primary Examiner* — Fabricio R Murillo Garcia
(74) *Attorney, Agent, or Firm* — Leydig, Voit & Mayer, Ltd.

(57) ABSTRACT

A wearable device is disclosed, including a microprocessor control unit, a first switch module, a Bluetooth module, and a multimedia module. The wearable device can be connected to a terminal device by using the Bluetooth module to share data, use data locally stored in the multimedia module, and monitor data corresponding to a preset event by using the microprocessor control unit. The wearable device integrates multiple functions, and connections between the modules can be switched according to an application scenario of the wearable device, to implement a quick transition between the functions, and to improve intelligence of man-machine interaction.

16 Claims, 3 Drawing Sheets

(56) References Cited

U.S. PATENT DOCUMENTS

| | | |
|---|---|---|
| 2014/0273858 A1 | 9/2014 | Panther et al. |
| 2015/0049591 A1 | 2/2015 | Adams et al. |
| 2015/0130685 A1* | 5/2015 | Kim .................. G06F 3/147 345/3.1 |
| 2015/0258371 A1 | 9/2015 | Tchao et al. |
| 2015/0334657 A1* | 11/2015 | Newham ............ H04W 76/023 455/41.2 |

FOREIGN PATENT DOCUMENTS

| | | |
|---|---|---|
| CN | 103229491 A | 7/2013 |
| CN | 203606933 U | 5/2014 |
| CN | 104361016 A | 2/2015 |
| EP | 2172249 A2 | 4/2010 |
| WO | 2012170924 A2 | 12/2012 |

* cited by examiner

WEARABLE DEVICE

CROSS-REFERENCE TO RELATED APPLICATIONS

This application is a National Stage of International Application No. PCT/CN2015/073411, filed on Feb. 28, 2015, which is hereby incorporated by reference in its entirety.

TECHNICAL FIELD

The present invention relates to wearable device technologies, and in particular, to a wearable device.

BACKGROUND

With development of smart devices, smart wearable devices are becoming more popular with users. Current wearable devices mainly include smart bands, smartwatches, smart necklaces, and the like.

In the prior art, generally all wearable devices include a Bluetooth module. A wearable device can track a status of a user during exercise, sleep and so on, and can also be wirelessly connected to a mobile phone by means of Bluetooth, to transmit detected information to the mobile phone.

However, prior-art wearable devices do not have diversified functions and cannot satisfy user requirements in different scenarios. That is, man-machine interaction of prior-art wearable devices is not intelligent enough, and user experience is poor.

SUMMARY

Embodiments of the present invention provide a wearable device, to resolve a problem that man-machine interaction of prior-art wearable devices is not intelligent enough.

A first aspect of the present invention provides a wearable device, including a microprocessor control unit, a first switch module, a Bluetooth module, and a multimedia module, where the Bluetooth module, the multimedia module, and the microprocessor control unit are all connected to the first switch module;

the Bluetooth module is configured to send a switch request to the first switch module according to a received scenario notification;

the first switch module is configured to establish a data transmission connection between the Bluetooth module and the multimedia module, or establish a data transmission connection between the Bluetooth module and the microprocessor control unit, according to the switch request; and the multimedia module is configured to store and play a multimedia file, and the microprocessor control unit is configured to monitor and store data corresponding to a preset event.

With reference to the first aspect, in a first possible implementation of the first aspect, a first general purpose input/output GPIO connection is further established between the Bluetooth module and the first switch module, and the Bluetooth module sends the switch request to the first switch module by using the first GPIO connection.

With reference to the first aspect or the first possible implementation of the first aspect, in a second possible implementation of the first aspect, the scenario notification is a multimedia module viewing request sent by a terminal device, and the switch request is a first switch request;

the Bluetooth module is specifically configured to: receive the multimedia module viewing request sent by the terminal device, and send the first switch request to the first switch module according to the multimedia module viewing request; and the first switch module is configured to establish the data transmission connection between the Bluetooth module and the multimedia module according to the first switch request.

With reference to the first aspect or the first possible implementation of the first aspect, in a third possible implementation of the first aspect, the scenario notification is a microprocessor-control-unit data synchronization request sent by a terminal device, and the switch request is a second switch request;

the Bluetooth module is specifically configured to: receive the microprocessor-control-unit data synchronization request sent by the terminal device, and send the second switch request to the first switch module according to the microprocessor-control-unit data synchronization request; and the first switch module is configured to establish the data transmission connection between the Bluetooth module and the microprocessor control unit according to the second switch request.

With reference to the first aspect or the first possible implementation of the first aspect, in a fourth possible implementation of the first aspect, the scenario notification is a preset-event occurrence notification sent by the microprocessor control unit, and the switch request is a third switch request;

a second GPIO connection is established between the Bluetooth module and the microprocessor control unit;

the microprocessor control unit is configured to send the preset-event occurrence notification to the Bluetooth module by using the second GPIO connection when detecting that a preset event occurs;

the Bluetooth module is specifically configured to: receive the preset-event occurrence notification sent by the microprocessor control unit, and send the third switch request to the first switch module according to the preset-event occurrence notification; and the first switch module is configured to establish the data transmission connection between the Bluetooth module and the microprocessor control unit according to the third switch request.

With reference to any one of the first aspect or the first to the fourth possible implementations of the first aspect, in a fifth possible implementation of the first aspect, the wearable device further includes a sound module and a second switch module, where the sound module is connected to the second switch module, and the second switch module is connected to the Bluetooth module, the multimedia module, and the microprocessor control unit;

the microprocessor control unit is configured to: receive selection information entered by a user, and send a control signal to the second switch module according to the selection information; and the second switch module is configured to establish a connection between the Bluetooth module and the sound module, or establish a connection between the multimedia module and the sound module, according to the control signal.

With reference to the fifth possible implementation of the first aspect, in a sixth possible implementation of the first aspect, the sound module includes a first channel unit and a second channel unit, and the second switch module includes a first channel switch unit and a second channel switch unit;

the first channel unit is connected to the first channel switch unit, and the second channel unit is connected to the second channel switch unit;

the first channel switch unit is connected to the Bluetooth module, the multimedia module, and the microprocessor control unit, and the second channel switch unit is connected to the Bluetooth module, the multimedia module, and the microprocessor control unit;

the microprocessor control unit is configured to: receive the selection information entered by the user, and send the control signal to the first channel switch unit and the second channel switch unit according to the selection information;

the first channel switch unit is configured to establish a connection between the Bluetooth module and the first channel unit, or establish a connection between the multimedia module and the first channel unit, according to the control signal; and the second channel switch unit is configured to establish a connection between the Bluetooth module and the second channel unit, or establish a connection between the multimedia module and the second channel unit, according to the control signal.

With reference to the first aspect, in a seventh possible implementation of the first aspect, the wearable device further includes an interface module and a third switch module, where the interface module is connected to the third switch module, and the third switch module is connected to the Bluetooth module, the multimedia module, and the microprocessor control unit, where the third switch module initially establishes a connection between the Bluetooth module and the interface module;

a second GPIO connection is further established between the Bluetooth module and the microprocessor control unit;

the Bluetooth module is configured to: receive upgrade information sent by a terminal device by using the interface module, determine an upgrade type of the upgrade information, and send the upgrade type to the microprocessor control unit by using the second GPIO connection; and the microprocessor control unit is configured to control, according to the upgrade type, the third switch module whether to switch the connection between the Bluetooth module and the interface module to a connection between the multimedia module and the interface module, where the upgrade type includes: upgrading the Bluetooth module, upgrading the microprocessor control unit, or upgrading the multimedia module.

With reference to the seventh possible implementation of the first aspect, in an eighth possible implementation of the first aspect, if the upgrade type is upgrading the multimedia module, the microprocessor control unit is specifically configured to control the third switch module to switch the connection between the Bluetooth module and the interface module to the connection between the multimedia module and the interface module.

With reference to the eighth possible implementation of the first aspect, in a ninth possible implementation of the first aspect, a third GPIO connection is further established between the multimedia module and the microprocessor control unit; and the microprocessor control unit is configured to: receive upgrade completion information sent by the multimedia module by using the third GPIO connection, and control, according to the upgrade completion information, the third switch module to switch the connection between the multimedia module and the interface module to the connection between the Bluetooth module and the interface module.

With reference to the fifth or the sixth possible implementation of the first aspect, in a tenth possible implementation of the first aspect, the Bluetooth module is connected to the sound module;

the Bluetooth module is configured to: convert to-be-played information of the wearable device into voice information in a preset language, and send the voice information in the preset language to the sound module; and the sound module is configured to play the voice information in the preset language to the user.

With reference to any one of the first aspect or the first to the tenth possible implementations of the first aspect, in an eleventh possible implementation of the first aspect, the wearable device is a necklace-type wearable device or a wristband-type wearable device.

With reference to the eleventh possible implementation of the first aspect, in a twelfth possible implementation of the first aspect, two ends of the necklace-type wearable device are respectively connected to a first channel headset and a second channel headset.

The wearable device provided in the embodiments of the present invention includes a Bluetooth module and a multimedia module. Therefore, the wearable device not only can be connected to another terminal device by using the Bluetooth module to exchange data, but also can use data locally stored in the multimedia module; and additionally, can monitor data corresponding to a preset event by using a microprocessor control unit. In this way, the wearable device integrates multiple functions, to provide more experience for a user. In addition, the Bluetooth module sends a switch request to a first switch module according to a received scenario notification, and according to a switch request, the first switch module establishes a data transmission connection between the Bluetooth module and the multimedia module, or establishes a data transmission connection between the Bluetooth module and the microprocessor control unit. Therefore, connections between the internal modules can be dynamically switched according to specific application scenarios of the wearable device, and functions can be quickly transformed. This greatly improves intelligence of man-machine interaction, better satisfies a user requirement, and improves user experience.

BRIEF DESCRIPTION OF DRAWINGS

To describe the technical solutions in the embodiments of the present invention or in the prior art more clearly, the following briefly describes the accompanying drawings required for describing the embodiments or the prior art. Apparently, the accompanying drawings in the following description show some embodiments of the present invention, and persons of ordinary skill in the art may still derive other drawings from these accompanying drawings without creative efforts.

DESCRIPTION OF EMBODIMENTS

To make the objectives, technical solutions, and advantages of the embodiments of the present invention clearer, the following clearly and completely describes the technical solutions in the embodiments of the present invention with reference to the accompanying drawings in the embodiments of the present invention. Apparently, the described embodiments are some but not all of the embodiments of the present invention. All other embodiments obtained by persons of ordinary skill in the art based on the embodiments of the present invention without creative efforts shall fall within the protection scope of the present invention.

Figure 1:
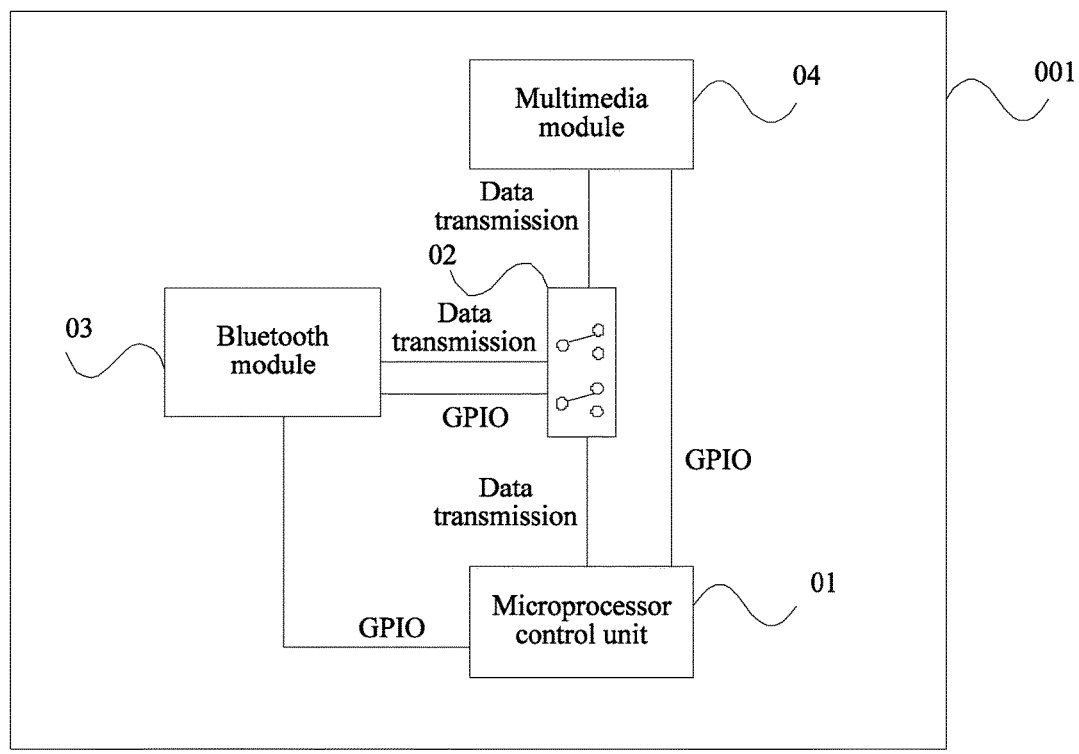
FIG. 1 is a schematic structural diagram of Embodiment 1 of a wearable device according to the present invention.

FIG. 1 is a schematic structural diagram of Embodiment 1 of a wearable device according to the present invention. As shown in FIG. 1, the wearable device 001 includes a microprocessor control unit (Microprocessor Control Unit, MCU for short) 01, a first switch module 02, a Bluetooth module 03, and a multimedia module 04.

The Bluetooth module 03, the multimedia module 04, and the microprocessor control unit 01 are all connected to the first switch module 02.

The Bluetooth module 03 is configured to send a switch request to the first switch module 02 according to a received scenario notification.

The first switch module 02 is configured to establish a data transmission connection between the Bluetooth module 03 and the multimedia module 04, or establish a data transmission connection between the Bluetooth module 03 and the microprocessor control unit 01, according to the switch request.

The data transmission connection may be a universal asynchronous receiver/transmitter (Universal Asynchronous Receiver/Transmitter, UART for short) connection. The UART connection is mainly used to transmit data between the modules. Certainly, the present invention is not limited to the UART protocol, and the connection may be established by using another protocol.

In a specific implementation process, for example, in an initial state, a data transmission connection is established between the first switch module 02 and the Bluetooth module 03, a data transmission connection is established between the first switch module 02 and the multimedia module 04, and a data transmission connection is established between the first switch module 02 and the microprocessor control unit 01. The first switch module 02 switches an internal switch according to a switch request, to connect the Bluetooth module 03 to the multimedia module 04, or connect the Bluetooth module 02 to the microprocessor control unit 01, thereby establishing the data transmission connection between the Bluetooth module 03 and the multimedia module 04 or the data transmission connection between the Bluetooth module 02 and the microprocessor control unit 01.

The multimedia module 04 is configured to store and play a multimedia file. That is, the wearable device 001 may locally store and play multimedia files. Formats of the multimedia files may be Moving Picture Experts Group Audio Layer 3 (MPEG-1 Audio Layer 3, MP3 for short), Windows Audio Volume (Windows Audio Volume, WAV for short), or Advanced Audio Coding (Advanced Audio Coding, AAC for short), but are not limited thereto. The multimedia files may alternatively be in music, text, image or other formats.

The microprocessor control unit 01 is configured to monitor and store data corresponding to a preset event. Specifically, the preset event may be an exercise event, and data corresponding to the exercise event may include various parameters such as exercise duration, an exercise distance, an exercise type, an exercise speed, and consumed calories. The preset event may alternatively be a health monitoring event, and data corresponding to the health monitoring event may include parameters such as a heart rate, blood pressure, and a sleeping status of a user, but is not limited thereto. Specifically, different preset events may be implemented by configuring different sensors on the microprocessor control unit 01.

The wearable device 001 provided in this embodiment of the present invention may establish a connection to a terminal device by using the Bluetooth module 03. The terminal device may be a mobile terminal such as a mobile phone or a tablet computer. An application program (Application Program, APP for short) corresponding to the wearable device 001 may be installed on the terminal device. In this way, the user can control the wearable device 001 by using the terminal device, or data can be synchronized between the wearable device 001 and the terminal device. The corresponding APP on the terminal device may analyze data obtained by the wearable device 001, for example, analyze various parameters such as exercise information and health information of the user. The wearable device 001 may also share some data of the terminal device, for example, play a multimedia file stored on the terminal device.

The Bluetooth module 03 may receive a scenario notification sent by the terminal device by using a Bluetooth connection or a scenario notification sent by another module in the wearable device 001, identify a corresponding scenario according to the scenario notification, and generate a corresponding switch request. For example, in some scenarios, if data in the multimedia module needs to be obtained, the first switch module 02 is requested to establish a connection between the Bluetooth module 03 and the multimedia module 04. In some scenarios, if data in the microprocessor control unit 01 needs to be obtained or the microprocessor control unit 01 needs to perform some operations, a connection between the Bluetooth module 03 and the microprocessor control unit 01 is established. Examples of scenarios are not enumerated herein.

Because the wearable device provided in this embodiment includes the Bluetooth module and the multimedia module, the wearable device not only can be connected to another terminal device by using the Bluetooth module to exchange data, but also can use data locally stored in the multimedia module, as well as monitor data corresponding to a preset event by using the microprocessor control unit. That is, the wearable device integrates multiple functions, providing more extensive experience for a user. In addition, the Bluetooth module sends a switch request to the first switch module according to a received scenario notification, and the first switch module establishes a data transmission connection between the Bluetooth module and the multimedia module, or establishes a data transmission connection between the Bluetooth module and the microprocessor control unit, according to a switch request. That is, connections between the internal modules can be dynamically switched according to a specific application scenario of the wearable device, thereby implementing a quick transition between the functions. This greatly improves intelligence of man-machine interaction, and better satisfies a user requirement.

Referring to FIG. 1, based on the foregoing embodiment, a first general purpose input/output (General Purpose Input Output, GPIO for short) connection is further established between the Bluetooth module 03 and the first switch module 02. The Bluetooth module 03 sends the switch request to the first switch module 02 by using the first GPIO connection.

Based on the foregoing embodiment, there may be a variety of scenario notifications. Specifically, the following scenarios may be included:

(1) The scenario notification is a multimedia module viewing request sent by a terminal device, and the switch request is a first switch request.

Correspondingly, the Bluetooth module 03 is specifically configured to: receive the multimedia module viewing request sent by the terminal device, and send the first switch request to the first switch module 02 according to the multimedia module viewing request.

The first switch module 02 establishes the data transmission connection between the Bluetooth module 03 and the multimedia module 04 according to the first switch request. In this way, the Bluetooth module 03 can read data in the multimedia module 04, and feed back related data to the terminal device.

Specifically, by using the Bluetooth module 03, the terminal device may view a file directory in the multimedia module 04, or may view various information such as a file name and a file type.

(2) The scenario notification is a microprocessor-control-unit data synchronization request sent by a terminal device, and the switch request is a second switch request.

Correspondingly, the Bluetooth module 03 is specifically configured to: receive the microprocessor-control-unit data synchronization request sent by the terminal device, and send the second switch request to the first switch module 02 according to the microprocessor-control-unit data synchronization request.

The first switch module 02 is configured to establish the data transmission connection between the Bluetooth module 03 and the microprocessor control unit 01 according to the second switch request. In this way, the Bluetooth module 03 can read data from the microprocessor control unit 01, and feed back the data to the terminal device for synchronization.

(3) The scenario notification is a preset-event occurrence notification sent by the microprocessor control unit, and the switch request is a third switch request.

Correspondingly, a second GPIO connection is further established between the Bluetooth module 03 and the microprocessor control unit 01. The microprocessor control unit 01 may send some notification messages to the Bluetooth module 03 by using the second GPIO connection.

Specifically, the microprocessor control unit 01 sends the preset-event occurrence notification to the Bluetooth module 03 by using the second GPIO connection when detecting that a preset event occurs. Specifically, the microprocessor control unit 01 may be preset to monitor at least one preset event.

The Bluetooth module 03 is specifically configured to: receive the preset-event occurrence notification sent by the microprocessor control unit 01, and send the third switch request to the first switch module 02 according to the preset-event occurrence notification.

The first switch module 02 is configured to establish the data transmission connection between the Bluetooth module 03 and the microprocessor control unit 01 according to the third switch request.

Specifically, the preset-event occurrence notification may be an exercise goal achievement notification, an exercise parameter monitoring notification, a device status notification, or the like. The user may preset an exercise goal to "walking 1500 steps every day" by using the APP on the connected terminal. In this case, when the microprocessor control unit 01 detects that the user have walked 1500 steps that day, indicating that the exercise goal is achieved, the microprocessor control unit 01 sends an exercise goal achievement notification to the Bluetooth module 03.

Certainly, the present invention is not limited to the foregoing scenarios. Various application scenarios may be specifically configured, and connections between the modules may be dynamically switched according to different scenario requirements.

Figure 2:
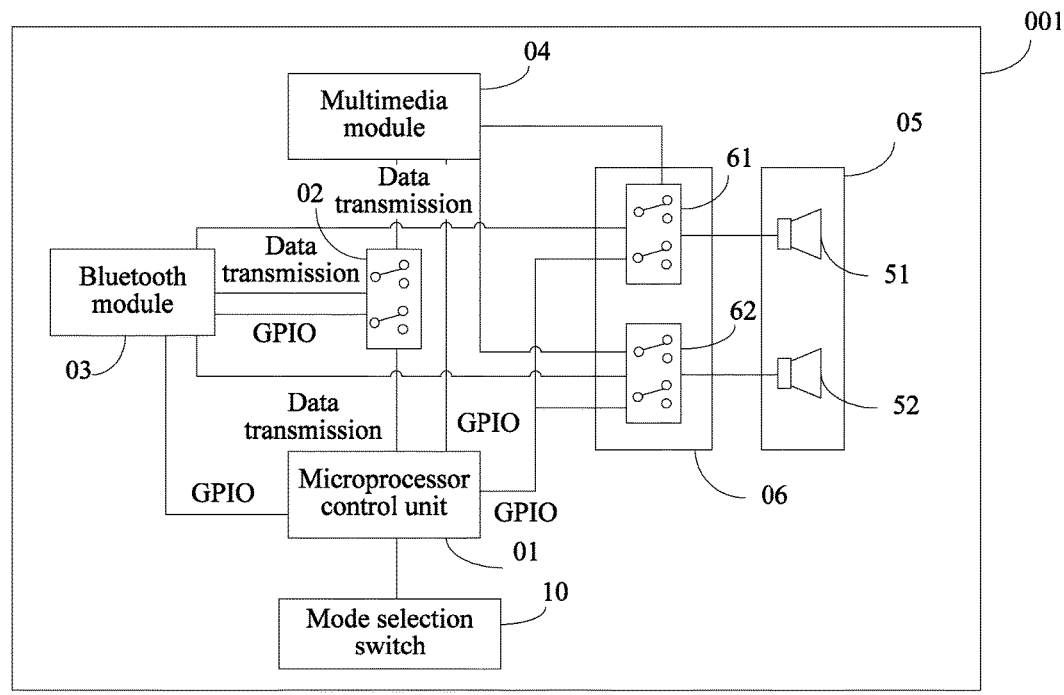
FIG. 2 is a schematic structural diagram of Embodiment 2 of a wearable device according to the present invention.

FIG. 2 is a schematic structural diagram of Embodiment 2 of a wearable device according to the present invention. As shown in FIG. 2, based on FIG. 1, the wearable device 001 may further include a sound module 05 and a second switch module 06.

The sound module 05 is connected to the second switch module 06. The second switch module 06 is connected to the Bluetooth module 03, the multimedia module 04, and the microprocessor control unit 01.

The microprocessor control unit 01 is further configured to: receive selection information entered by a user, and send a control signal to the second switch module 06 according to the selection information.

The second switch module 06 is configured to connect the Bluetooth module 03 to the sound module 05, or connect the multimedia module 04 to the sound module 05, according to the control signal.

The selection information may be information about selection of a multimedia file play mode by the user. For example, the user may select a Bluetooth mode or a local multimedia mode.

During specific implementation, a mode selection switch 10 may be disposed on the wearable device 001, for the user to select the Bluetooth mode or the local multimedia mode. Alternatively, the Bluetooth mode or the local multimedia mode may be selected by using the APP on the terminal device that is connected to the wearable device 001 by means of Bluetooth.

If the user selects the local multimedia mode, the multimedia module 04 plays the locally stored multimedia file, and the user can enjoy the multimedia file that is locally stored in the multimedia module 04. If the user selects the Bluetooth mode, the user uses the Bluetooth module 03 to enjoy a multimedia file stored on the connected terminal device. This enables the user to freely select the multimedia file play mode according to a requirement and preferences of the user, and connections between the internal modules can be quickly switched.

The sound module 05 may include a speaker and a headset jack, and play a sound of an audio multimedia file by using a headset or the speaker according to whether there is a headset plugged in.

Still referring to FIG. 2, based on the foregoing embodiment, the sound module 05 may include a first channel unit 51 and a second channel unit 52. Correspondingly, the second switch unit 06 may include a first channel switch unit 61 and a second channel switch unit 62. The first channel unit 51 is connected to the first channel switch unit 61, and the second channel unit 52 is connected to the second channel switch unit 62. The first channel unit 51 is connected to the Bluetooth module 03, the multimedia module 04, and the microprocessor control unit 01, and the second channel switch unit 62 is connected to the Bluetooth module 03, the multimedia module 04, and the microprocessor control unit 01.

The microprocessor control unit 01 is configured to: receive the selection information entered by the user, and send the control signal to the first channel switch unit 61 and the second channel switch unit 62 according to the selection information.

The selection information may be information about selection of a multimedia file play mode by the user. For example, the user may select a Bluetooth mode or a local multimedia mode.

Correspondingly, the first channel switch unit 61 is configured to connect the Bluetooth module 03 to the first channel unit 51, or connect the multimedia module 04 to the first channel unit 51, according to the control signal.

The second channel switch unit 62 is configured to connect the Bluetooth module 03 to the second channel switch unit 62, or connect the multimedia module 04 to the second channel switch unit 62, according to the control signal.

It should be noted that, the first channel switch unit 61 and the second channel switch unit 62 perform a same action according to a same control signal. That is, when the first channel switch unit 61 connects the Bluetooth module 03 to the first channel unit 51, the second channel switch unit 62 connects the Bluetooth module 03 to the second channel switch unit 62; when the first channel switch unit 61 connects the multimedia module 04 to the first channel unit 51, the second channel switch unit 62 connects the multimedia module 04 to the second channel switch unit 62.

Specifically, for example, when the user selects the Bluetooth mode, the microprocessor control unit 01 sends a first control signal to the first channel switch unit 61 and the second channel switch unit 62; the first channel switch unit 61 connects the Bluetooth module 03 to the first channel unit 51 according to the first control signal, and the second channel switch unit 62 connects the Bluetooth module 03 to the second channel switch unit 62 according to the first control signal.

When the user selects the local multimedia mode, the microprocessor control unit 01 sends a second control signal to the first channel switch unit 61 and the second channel switch unit 62; the first channel switch unit 61 connects the multimedia module 04 to the first channel unit 51 according to the second control signal, and the second channel switch unit 62 connects the multimedia module 04 to the second channel switch unit 62 according to the second control signal.

The wearable device 001 provided in this embodiment includes two channels, allowing the user to better enjoy an audio multimedia file.

Figure 3:
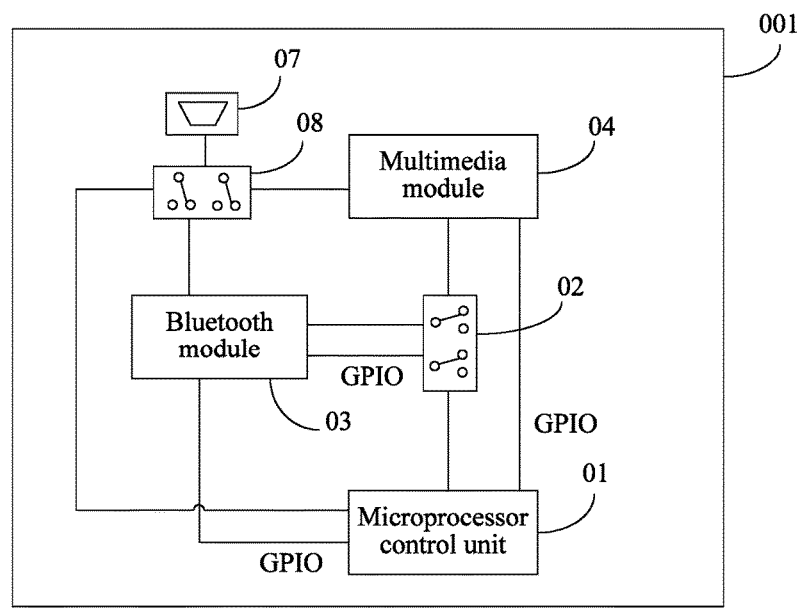
FIG. 3 is a schematic structural diagram of Embodiment 3 of a wearable device according to the present invention.

FIG. 3 is a schematic structural diagram of Embodiment 3 of a wearable device according to the present invention. As shown in FIG. 3, the wearable device 001 further includes an interface module 07 and a third switch module 08.

The interface module 07 is connected to the third switch module 08, and the third switch module 08 is connected to the Bluetooth module 03, the multimedia module 04, and the microprocessor control unit 01. The third switch module 08 initially establishes a connection between the Bluetooth module 03 and the interface module 07. That is, during power-on, an initial state is that the third switch module 08 switches to a state in which the Bluetooth module 03 is connected to the interface module 07, so that the terminal device connected to the wearable device 001 by using Bluetooth sends information to the wearable device.

A second GPIO connection is further established between the Bluetooth module 03 and the microprocessor control unit 01.

The Bluetooth module 03 receives upgrade information sent by the terminal device by using the interface module 07, determines an upgrade type of the upgrade information, and sends the upgrade type to the microprocessor control unit 01 by using the second GPIO connection.

The microprocessor control unit 01 controls, according to the upgrade type, the third switch module 03 whether to switch "the connection between the Bluetooth module 03 and the interface module 07" to "a connection between the multimedia module 04 and the interface module 07".

The upgrade type includes: upgrading the Bluetooth module, upgrading the microprocessor control unit, or upgrading the multimedia module.

Generally, if the upgrade type is upgrading the Bluetooth module or upgrading the microprocessor control unit, the switching is not performed. That is, the connection between the Bluetooth module 03 and the interface module 07 is maintained.

If the upgrade type is upgrading the multimedia module, the microprocessor control unit 01 controls the third switch module 08 to switch "the connection between the Bluetooth module 03 and the interface module 07" to "the connection between the multimedia module 04 and the interface module 07". In this way, the multimedia module 04 receives the upgrade information by using the interface module 07, and is upgraded according to the upgrade information.

The upgrade information carries an upgrade package. The upgrade package may be provided by the APP corresponding to the wearable device 001 on the terminal device, and more specifically, is provided by a background server of the APP.

Based on the foregoing embodiment, a third GPIO connection is further established between the multimedia module 04 and the microprocessor control unit 01.

The microprocessor control unit 01 receives upgrade completion information sent by the multimedia module 04 by using the third GPIO connection, and controls, according to the upgrade completion information, the third switch module 08 to switch the connection between the multimedia module 04 and the interface module 07 to the connection between the Bluetooth module 03 and the interface module 07, that is, to restore the initial connection state.

In another embodiment, the Bluetooth module 03 may be connected to the sound module 05. The Bluetooth module 03 converts to-be-played information of the wearable device 001 into voice information in a preset language, and sends the voice information in the preset language to the sound module 05. The sound module 05 plays the voice information in the preset language to the user.

In a specific implementation process, the Bluetooth module 03 may integrate a text to speech (Text To Speech, TTS for short) algorithm and a multilingual voice package. The user may select in advance, on the wearable device 001, a play language as the preset language by using a button, or select a play language as the preset language by using the corresponding APP on the terminal device. The Bluetooth module 03 converts to-be-played information of the wearable device 001 into the voice information in the preset language by using the TTS algorithm according to the preset language and the multilingual voice package, for playing by the sound module 05.

The to-be-played information may include status information of the wearable device 001, for example, a Bluetooth-connected state, a Bluetooth-disconnected state, a power-on/power-off state, and a battery level, and may further include user exercise information, user health information, and the like that are monitored by the wearable device 001, for example, information about calories consumed by the user, exercise duration information, blood pressure information, and heart rate information.

Figure 4:
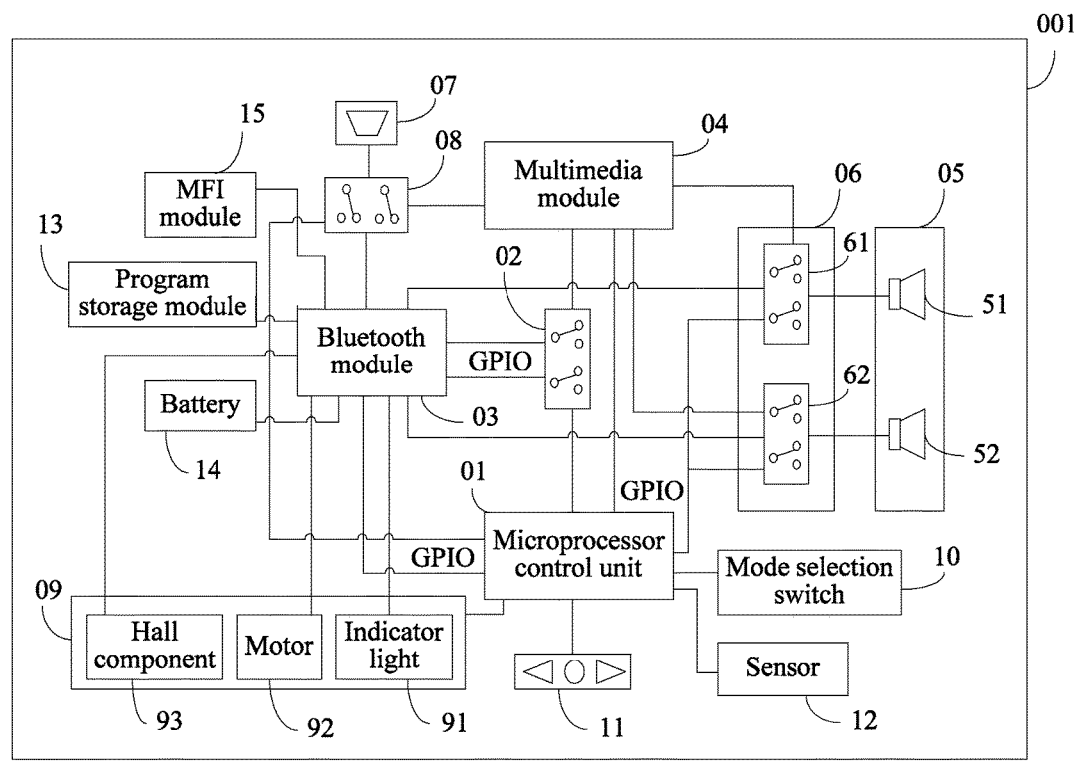
FIG. 4 is a schematic structural diagram of Embodiment 4 of a wearable device according to the present invention.

FIG. 4 is a schematic structural diagram of Embodiment 4 of a wearable device according to the present invention. FIG. 4 is a schematic circuit diagram of a complete wearable device 001. Certainly, the present invention is not limited thereto. As shown in FIG. 4, the wearable device may further include an event reminder unit 09, configured to remind a user of different states of the wearable device.

More specifically, the event reminder unit 09 may include an indicator light 91, a motor 92, and a Hall (Hall) component 93.

The indicator light 91 is connected to the Bluetooth module 03 and the microprocessor control unit 01, and may remind the user of different states by using different colors or different flickering frequencies. For example, different colors are used to remind the user that the wearable device is at a low battery level, that the wearable device is already Bluetooth-connected, and so on. The indicator light may be a light emitting diode (Light Emitting Diode, LED for short) light.

The motor 92 is connected to the Bluetooth module 03, and can cause the wearable device 001 to vibrate, to remind the user of some preset events by means of vibration, for example, an alarm clock reminder, or an exercise goal achievement reminder.

The Hall component 93 is connected to the Bluetooth module 03, and may be configured to detect whether headsets connected to the wearable device 001 are in a contact state. If the headsets are in the contact state, the device is on stand-by, and only monitors a call and/or records an exercise state, with other functions being disabled, so as to reduce power consumption of the device. If the headsets are in a separate state, functions such as answering a call and listening to music can be performed.

Further, the wearable device 001 may be a necklace-type wearable device or a wristband-type wearable device, but is not limited thereto. The wearable device 001 may alternatively be a glasses-type wearable device, an earring-type wearable device, or the like.

For the necklace-type wearable device, two ends of the necklace-type wearable device may be respectively connected to a first channel headset and a second channel headset. In a specific implementation process, the first channel headset and the second channel headset may be respectively connected to the corresponding first channel unit and second channel unit, to exploit the advantage that the wearable device provided in the present invention includes two channels. Compared with a wristband, headsets are directly disposed at two ends of the necklace, and the necklace is easier to wear and use for a user, without affecting exercise of the user. A wristband is usually provided with a monaural Bluetooth headset, so as not to affect exercise of the user.

Further, referring to FIG. 4, the wearable device 001 may further include an adjustment button 11. The adjustment button 11 is connected to the microprocessor control unit 01. By operating the adjustment button 11, the user can control power on/off of the wearable device 001, and can adjust a volume level during playing of a multimedia file by the wearable device 001.

The wearable device 001 may further include a sensor 12. The sensor 12 is connected to the microprocessor control unit 01, and is configured to monitor a preset event under the control of the microprocessor control unit 01. During specific implementation, the microprocessor control unit 01 may be connected to multiple different sensors, to implement monitoring of different events.

The wearable device 001 may further include a program storage module 13, which is connected to the Bluetooth module 03 and is configured to store a program necessary for the wearable device 001.

The wearable device 001 may further include a battery 14, which may be connected to the Bluetooth module 04 and is configured to supply power to the wearable device 001.

To connect to a device from Apple Inc., an MFI (Made for iOS) module 15 may be further disposed on the wearable device 001. The MFI module 15 is connected to the Bluetooth module 03, and is configured to connect the wearable device to a device from Apple Inc., such as an iPhone, an iPad, or an iPod.

Certainly, according to the wearable device provided in this embodiment of the present invention, connections between modules can be flexibly switched, thereby achieving integration of multiple functions of the wearable device. However, the wearable device is not limited to the foregoing functions, and another component may be added according to a specific requirement. For example, to expand storage space of the multimedia module 04, a memory card slot connected to the multimedia module 04 may be further provided. In this way, a memory card may be installed according to a user requirement to expand storage space.

Finally, it should be noted that, the foregoing embodiments are merely intended for describing the technical solutions of the present invention other than limiting the present invention. Although the present invention is described in detail with reference to the foregoing embodiments, persons of ordinary skill in the art should understand that they may still make modifications to the technical solutions described in the foregoing embodiments or make equivalent replacements to some technical features thereof, without departing from the scope of the technical solutions of the embodiments of the present invention.

What is claimed is:

1. A wearable device, comprising: a microprocessor, a first switch, a Bluetooth element, and a multimedia element, wherein the Bluetooth element, the multimedia element, and the microprocessor are all connected to the first switch;

the Bluetooth element is configured to send a switch request to the first switch according to a received scenario notification;

the first switch is configured to selectively establish a data transmission connection between a) the Bluetooth element and the multimedia element, and b) a data transmission connection between the Bluetooth element and the microprocessor, according to the switch request; and the multimedia element is configured to store and play a multimedia file, and the microprocessor is configured to monitor and store data corresponding to a preset event;

wherein the scenario notification is a preset-event occurrence notification sent by the microprocessor, and the switch request is a second switch request;

a general purpose input/output (GPIO) connection is established between the Bluetooth element and the microprocessor;

the microprocessor is configured to send the preset-event occurrence notification to the Bluetooth element using the GPIO connection when detecting that a preset event occurs;

the Bluetooth element is configured to: receive the preset-event occurrence notification sent by the microprocessor, and send the second switch request to the first switch according to the preset-event occurrence notification; and the first switch is configured to establish the data transmission connection between the Bluetooth element and the microprocessor according to the second switch request.

2. The wearable device according to claim 1, wherein a first general purpose input/output (GPIO) connection is further established between the Bluetooth element and the first switch, and the Bluetooth element sends the switch request to the first switch using the first GPIO connection.

3. The wearable device according to claim 2, wherein the scenario notification is a multimedia element viewing request sent by a terminal device, and the switch request is a first switch request;

the Bluetooth element is configured to: receive the multimedia element viewing request sent by the terminal device, and send the first switch request to the first switch according to the multimedia element viewing request; and the first switch is configured to establish the data transmission connection between the Bluetooth element and the multimedia element according to the first switch request.

4. The wearable device according to claim 2, wherein the scenario notification is a microprocessor data synchronization request sent by a terminal device, and the switch request is a third switch request;

the Bluetooth element is configured to: receive the microprocessor data synchronization request sent by the terminal device, and send the third switch request to the first switch according to the microprocessor data synchronization request; and the first switch is configured to establish the data transmission connection between the Bluetooth element and the microprocessor according to the third switch request.

5. The wearable device according to claim 4, wherein the Bluetooth element is connected to a sound player;

the Bluetooth element is configured to: convert to-be-played information of the wearable device into voice information in a preset language, and send the voice information in the preset language to the sound player; and the sound player is configured to play the voice information in the preset language to the user.

6. The wearable device according to claim 2, wherein the scenario notification is a preset-event occurrence notification sent by the microprocessor, and the switch request is a third switch request;

a second GPIO connection is established between the Bluetooth element and the microprocessor;

the microprocessor is configured to send the preset-event occurrence notification to the Bluetooth element using the second GPIO connection when detecting that a preset event occurs;

the Bluetooth element is configured to: receive the preset-event occurrence notification sent by the microprocessor, and send the third switch request to the first switch according to the preset-event occurrence notification; and the first switch is configured to establish the data transmission connection between the Bluetooth element and the microprocessor according to the third switch request.

7. The wearable device according to claim 1, wherein the scenario notification is a multimedia element viewing request sent by a terminal device, and the switch request is a first switch request;

the Bluetooth element is configured to: receive the multimedia element viewing request sent by the terminal device, and send the first switch request to the first switch according to the multimedia element viewing request; and the first switch is configured to establish the data transmission connection between the Bluetooth element and the multimedia element according to the first switch request.

8. The wearable device according to claim 1, wherein the scenario notification is a microprocessor data synchronization request sent by a terminal device, and the switch request is a third switch request;

the Bluetooth element is configured to: receive the microprocessor data synchronization request sent by the terminal device, and send the third switch request to the first switch according to the microprocessor data synchronization request; and the first switch is configured to establish the data transmission connection between the Bluetooth element and the microprocessor according to the third switch request.

9. The wearable device according to claim 1, further comprising a sound player and a second switch, wherein the sound player is connected to the second switch, and the second switch is connected to the Bluetooth element, the multimedia element, and the microprocessor;

the microprocessor is configured to: receive selection information entered by a user, and send a control signal to the second switch according to the selection information; and the second switch is configured to establish a connection between the Bluetooth element and the sound player, or establish a connection between the multimedia element and the sound player, according to the control signal.

10. The wearable device according to claim 9, wherein the sound player comprises a first channel unit and a second channel unit, and the second switch comprises a first channel switch and a second channel switch;

the first channel unit is connected to the first channel switch, and the second channel unit is connected to the second channel switch;

the first channel switch is connected to the Bluetooth element, the multimedia element, and the microprocessor, and the second channel switch is connected to the Bluetooth element, the multimedia element, and the microprocessor;

the microprocessor is configured to: receive the selection information entered by the user, and send the control signal to the first channel switch and the second channel switch according to the selection information;

the first channel switch is configured to establish a connection between the Bluetooth element and the first channel unit, or establish a connection between the multimedia element and the first channel unit, according to the control signal; and the second channel switch is configured to establish a connection between the Bluetooth element and the second channel unit, or establish a connection between the multimedia element and the second channel unit, according to the control signal.

11. The wearable device according to claim 1, wherein the Bluetooth element is connected to a sound player;

the Bluetooth element is configured to: convert to-be-played information of the wearable device into voice information in a preset language, and send the voice information in the preset language to the sound player; and the sound player is configured to play the voice information in the preset language to the user.

12. The wearable device according to claim 1, wherein the wearable device is a necklace-type wearable device or a wristband-type wearable device.

13. The wearable device according to claim 12, wherein two ends of the necklace-type wearable device are respectively connected to a first channel headset and a second channel headset.

14. A wearable device, comprising: a microprocessor, a first switch, a Bluetooth element, and a multimedia element, wherein the Bluetooth element, the multimedia element, and the microprocessor are all connected to the first switch;

the Bluetooth element is configured to send a switch request to the first switch according to a received scenario notification;

the first switch is configured to selectively establish a data transmission connection between a) the Bluetooth element and the multimedia element, and b) a data transmission connection between the Bluetooth element and the microprocessor, according to the switch request; and the multimedia element is configured to store and play a multimedia file, and the microprocessor is configured to monitor and store data corresponding to a preset event, and further comprising an interface and a second switch, wherein the interface is connected to the second switch, and the second switch is connected to the Bluetooth element, the multimedia element, and the microprocessor, wherein the second switch initially establishes a connection between the Bluetooth element and the interface;

a general purpose input/output (GPIO) connection is further established between the Bluetooth element and the microprocessor;

the Bluetooth element is configured to: receive upgrade information sent by a terminal device using the interface, determine an upgrade type of the upgrade information, and send the upgrade type to the microprocessor using the GPIO connection; and the microprocessor is configured to control, according to the upgrade type, the second switch whether to switch the connection between the Bluetooth element and the interface to a connection between the multimedia element and the interface, wherein the upgrade type comprises: upgrading the Bluetooth element, upgrading the microprocessor, or upgrading the multimedia element.

15. The wearable device according to claim 14, wherein if the upgrade type is upgrading the multimedia element, the microprocessor is configured to control the second switch to switch the connection between the Bluetooth element and the interface to the connection between the multimedia element and the interface.

16. The wearable device according to claim 15, wherein a second GPIO connection is further established between the multimedia element and the microprocessor; and the microprocessor is configured to: receive upgrade completion information sent by the multimedia element using the second GPIO connection, and control, according to the upgrade completion information, the second switch to switch the connection between the multimedia element and the interface to the connection between the Bluetooth element and the interface.

* * * * *